United States Patent [19]
May

[11] Patent Number: 5,925,005
[45] Date of Patent: Jul. 20, 1999

[54] SMALL ANIMAL INTRAVENOUS RESTRAINT SPLINT

[75] Inventor: Paul E. May, Upatoi, Ga.

[73] Assignee: May Medical Products, Inc., Columbus, Ga.

[21] Appl. No.: 09/013,393

[22] Filed: Jan. 26, 1998

[51] Int. Cl.⁶ ........................................ A61F 5/00
[52] U.S. Cl. ........................ 602/6; 602/5; 602/20
[58] Field of Search .................. 602/5, 6, 20, 62; 128/845, 846, 877, 878, 880, 881; 119/817

[56] References Cited

U.S. PATENT DOCUMENTS

| | | | |
|---|---|---|---|
| Re. 32,335 | 1/1987 | Heck | 602/20 |
| 1,624,861 | 4/1927 | Dewey | 119/817 |
| 2,474,634 | 6/1949 | Mason | 602/5 |
| 3,256,880 | 6/1966 | Caypinar | 128/877 |
| 3,881,472 | 5/1975 | Lee | 602/6 |
| 4,361,143 | 11/1982 | Nelson | 602/23 |
| 4,489,716 | 12/1984 | Blackwood et al. | 602/20 |
| 4,505,270 | 3/1985 | Miles | 602/12 |
| 4,612,925 | 9/1986 | Bender | 602/5 X |
| 5,134,992 | 8/1992 | Campbell | 602/6 |

*Primary Examiner*—Richard J. Apley
*Assistant Examiner*—Denise M. Pothier
*Attorney, Agent, or Firm*—John C. Garvin, Jr.; Harold W. Hilton

[57] ABSTRACT

A veterinary medical leg splint for an animal. The leg splint includes a body having an elongated body portion. One end of the body portion is open to support the digital and metacarpal pads of the animal's foot therein. The other end of the elongated body portion is partially closed by an upstanding portion which is shaped to conform to the configuration of the animal's leg in the area of the elbow joint. The leg and splint are wrapped together to restrain the leg of the animal in the splint.

10 Claims, 4 Drawing Sheets

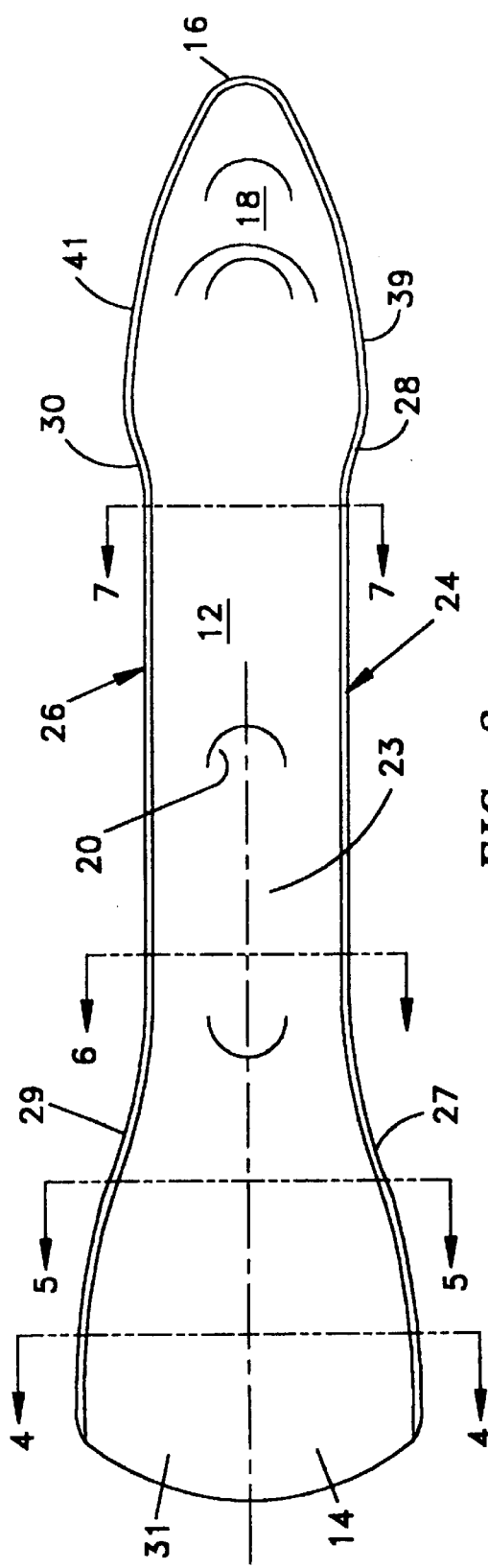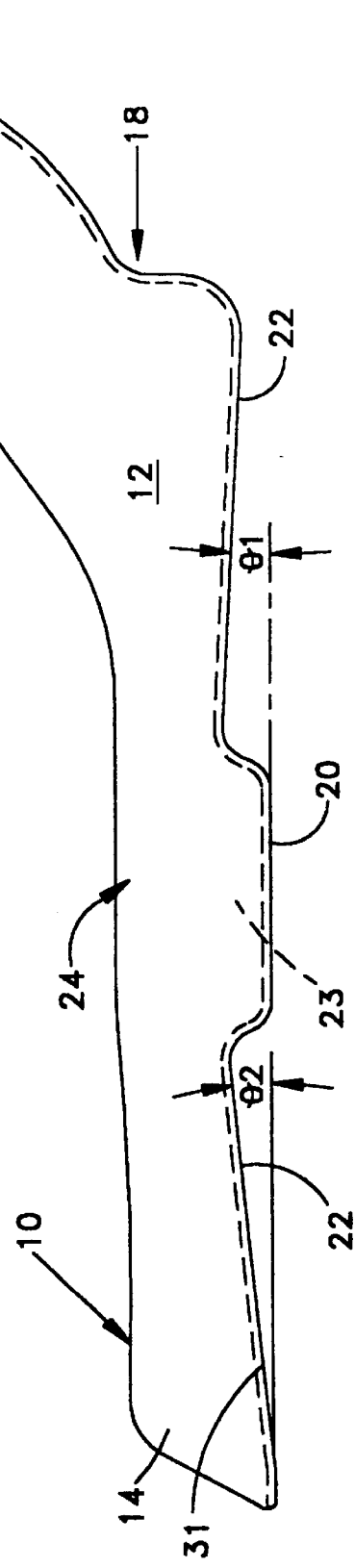

SMALL ANIMAL INTRAVENOUS RESTRAINT SPLINT

FIELD OF THE INVENTION

This invention relates generally to the administration of intravenous fluids to animals and more particularly to a splint for use on the leg of a small animal such as a cat or dog which retains the leg in a position which will permit uninterrupted intravenous fluid administration to the animal. The splint may be used to stabilize the leg for fracture repair and soft tissue injury.

BACKGROUND OF THE INVENTION

Intravenous administration of fluids to small animal patients is a frequent occurrence at many animal clinics. Typically, intravenous fluid is administered by inserting the intravenous needle or catheter in the cephalic vein (a large vein which travels up the cranial foreleg and upper leg of the animal). The needle or catheter, of course, is connected to the fluid source through a tube, as is well known in the art.

One problem which may occur during the intravenous administration of fluid to an animal, such as a cat or dog, is that even with the needle inserted in the cephalic vein, the animal tends to frequently pull their front legs under them into a sitting or sternal position. However, when the elbow is pulled back into such position and the angle between the foreleg and upper leg (radius-ulnar and humerus) at the elbow joint becomes acute (<90°) the blood flow in the vein is reduced and the IV fluids will stop flowing.

This is obviously a critical situation. The patient needs the fluids, drugs or blood but because of the positional change, the vein is no longer open and the patient does not receive the fluid it needs. To keep the fluids flowing, the angle at the elbow joint needs to be greater than 90°.

Veterinarians have had very limited options to use on their patients to correct the above noted problem related to fluid administration. One method involves placing a rolled up towel behind the elbow to keep the angle opened. This will work until the patient moves forward. Another method involves tying the animals leg to the cage door. This works, also, until the patient moves forward. The Cochran IV splint is a metal splint that is available and is disclosed in U.S. Pat. No. 4,440,159. It difficult to place on a patient after the IV is established and it is somewhat expensive. Movement by the patient allows the splint to slip out of alignment with the leg, thus defeating the purpose of the splint. Another device, disclosed in U.S. Pat. No. 4,505,270 uses a splint that is bolted to the cage door. This is a procedure that could result in a serious injury to the patient.

SUMMARY OF THE INVENTION

A splint designed to hold the elbow angle (angle between the foreleg and upper leg) of an animal open at a comfortable angle, greater than 90 degrees while administering intravenous fluids to the animal. The main feature of the splint is an elbow trap which prevents the leg from being drawn up the splint and supports the animal's leg at a comfortable angle and in slight extension without resisting the splint.

BRIEF DESCRIPTION OF THE DRAWINGS

FIG. 1 is an elevational view of the splint of the present invention.

FIG. 2 is a plan view of the splint of FIG. 1.

FIG. 8 is partially broken away to illustrate the wrapping generally used on the leg of the animal and, also, the wrapping used to secure the leg of the animal in the splint of the present invention.

DESCRIPTION OF THE PREFERRED EMBODIMENT

Figure 3:
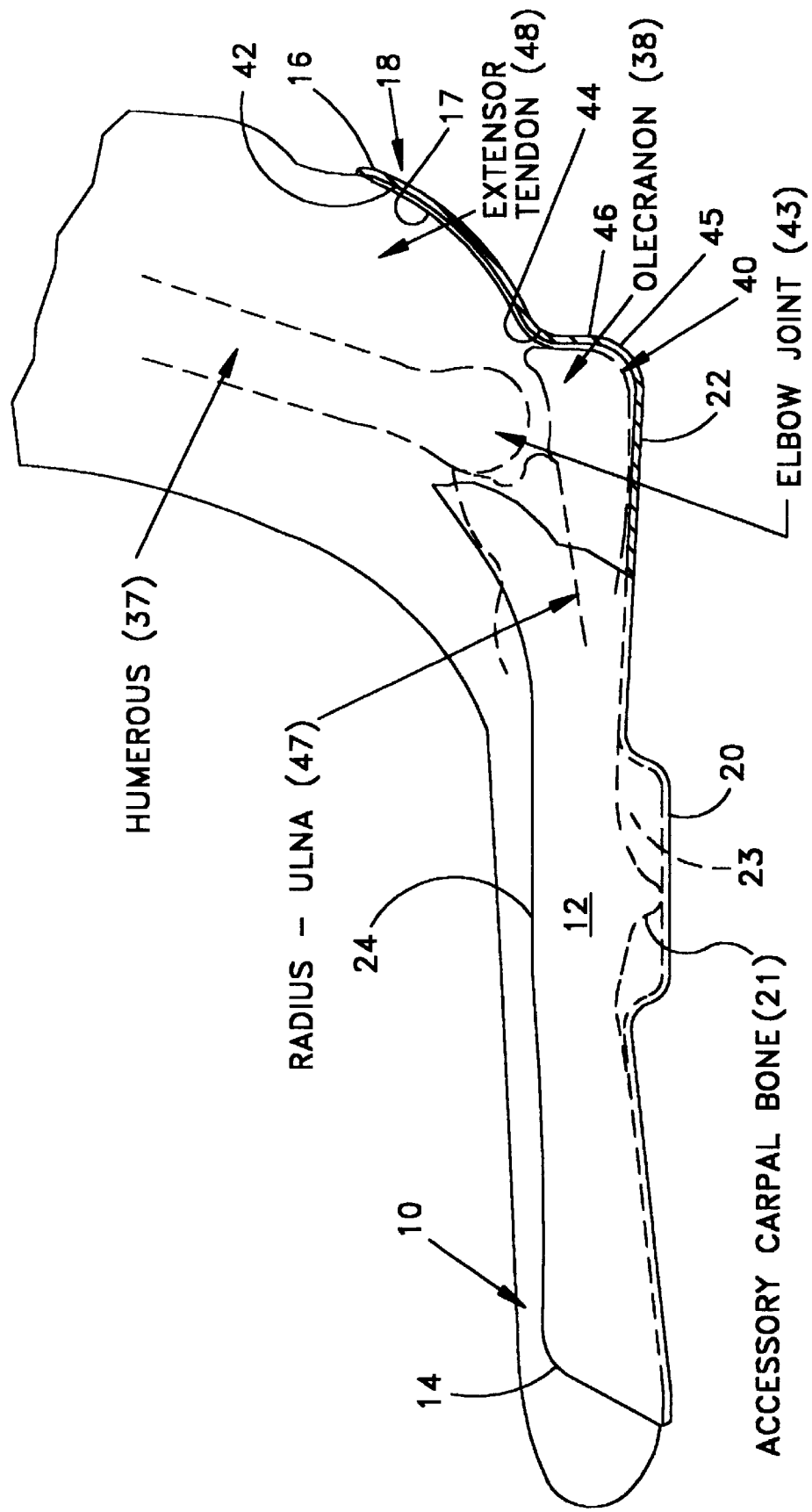
FIG. 3 is an elevational view similar to FIG. 1. The splint is partially broken away to illustrate the manner in which the leg of the animal at the elbow joint is supported in the elbow trap portion of the splint. No bandage windings are shown on the leg for the sake of clarity.

As seen in FIG. 1, the veterinary medical splint 10 includes an elongated body portion 12, preferably formed of plastic material. Body 12 includes an open, front end 14 and an upstanding rear end 16 joined by an intermediate sloped portion 18, hereinafter referred to as the "elbow trap" portion. The elbow trap serves to retain the leg of the patient in the splint as described hereinbelow. A downwardly depending protrusion or leg rest 20 protrudes from the lower surface of horizontally extending portion 22 of body 12. The downwardly depending protrusion 20 not only serves as a leg rest which maintains the leg of the animal at a comfortable angle denoted by $\Theta_1$ (FIG. 1), but also serves to protect the accessory carpal bone, denoted by numeral 21 (FIG. 3), and related tissue from undue pressure. The accessory carpal bone 21 is a small bone which extends downwardly from the palmar or caudal (inner) surface of the leg of the animal at a position which is proximal to and behind the metacarpal pad of the animal. The protrusion 20 has a hollow interior 23 therein to accept and support the accessory carpal bone.

As seen in FIG. 2, the splint includes a pair of diverging sides 24 and 26 which extend slightly inwardly as indicated at 28 and 30 and then slightly diverges longitudinally to points indicated at 27 and 29 and there expands outwardly to the open front end 14 of body 12. The lower inner surface 31 of body 12 at open front end 14 is widened as seen in FIG. 2 and at $W_1$ in FIGS. 4 and $W_2$ in FIG. 5. Surface 31 slopes slightly downwardly as indicated at $\Theta_2$ of FIG. 1. The slope at this point is typically approximately six degrees. The open front end 14 is widened so that the digital and metacarpal pads of the animal may be capable of being received therein. The angle, $\Theta_2$, is provided so that a degree of comfort may be afforded the animal at this point.

As seen in FIGS. 2 and 3, sides 24 and 26 include a pair of arcuate, raised portions 39 and 41 located adjacent elbow trap 18 for reasons explained hereinbelow.

Figure 4:
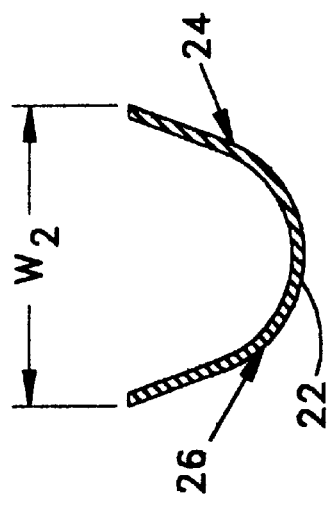
FIGS. 4–7 are sectional views taken along lines 4—4, 5—5, 6—6 and 7—7 of FIG. 2.

FIG. 4 is a sectional view taken along line 4—4 of FIG. 2.

Figure 5:
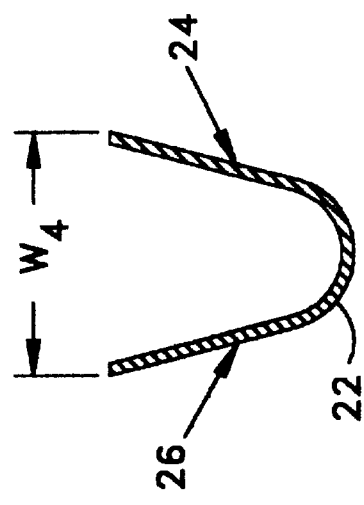

FIG. 5 is a sectional view taken along line 5—5 of FIG. 2.

Figure 6:
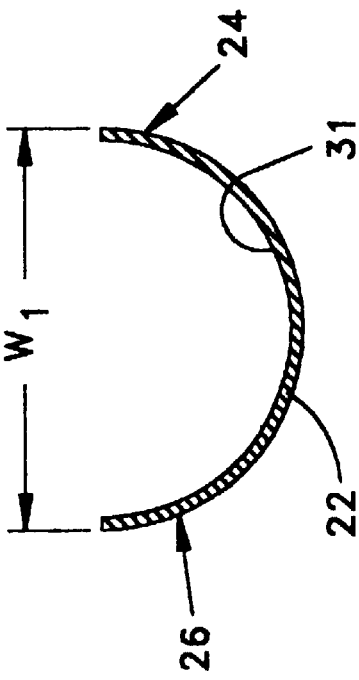

FIG. 6 is a sectional view taken along line 6—6 of FIG. 2.

Figure 7:
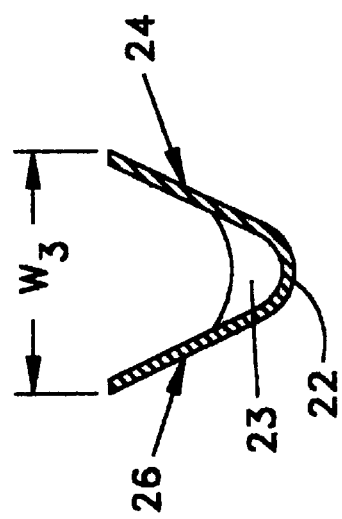

FIG. 7 is a sectional view taken along line 7—7 of FIG. 2.

FIGS. 4–7 are sectional views respectively taken along lines 4—4, 5—5, 6—6 and 7—7 of FIG. 2. As seen in FIG. 4, the front end portion 14 is provided with a substantially semi-circular configuration and also sides 24 and 26 are shown to be spaced apart by a width denoted as $W_1$. As previously stated, the pads of the animal are disposed to rest in front end section 14. FIG. 5 is a sectional view illustrating sides 24 and 26 converging slightly inwardly to a width denoted as $W_2$. FIG. 6 is a sectional view slightly forward of the midpoint of body 12 and illustrates sides 24 and 26 as having a width between them which is denoted by $W_3$. At this point, it should be noted that the configuration is substantially that of almost a "V" with lower surface 22 having a slightly rounded configuration. FIG. 7 is a sectional view along line 7—7 of body 12 and illustrates the width, $W_4$, between sides 24 and 26 as being slightly wider than $W_3$ of FIG. 6. Lower surface 22, at this point, is shown to have a substantially U-shaped configuration. The widths described above are variable and are provided to assure a substantially snug-fitting configuration which conforms to the anatomy of the legs of different sized animals. An example of the dimensions of one size of splint is:

$W_1$=2.25 inches
$W_2$=2.05 inches
$W_3$=1.55 inches
$W_4$=1.50 inches

As more clearly seen in FIG. 3, the elbow trap 18 engages the leg in the area of the olecranon 38 of the elbow 40 of the animal. To accomplish this, and as seen in FIG. 3, elbow trap 18 of body 12 includes an upper depression 42 formed in the inner surface 17 of the rear portion 16 of the splint. An inwardly extending rounded shoulder 44 is arranged proximal depression on surface 17 and a lower downwardly extending portion 46 extends downwardly to form a juncture 45 with horizontal surface 22 of body 12. When in place on the animals's leg, the olecranon 38 of the leg fits in juncture 45, and, shoulder 44 gently urges the extensor tendon of the leg, indicated at 48, slightly cranial. The relationship of the humerus 37, radius ulna 39, olecranon 38 and extensor tendon 48 relative to the elbow trap 18 is also illustrated in FIG. 3. The word "cranial" as used herein defines the direction toward the head of the animal. On an animal that stands on all fours the front or anterior of the leg is toward the head or cranial as set forth above In FIG. 3, the leg is illustrated without any bandage wrappings. This is done in order to more clearly illustrate the relationship of the leg's configuration relative to the configuration of the elbow trap of the splint.

Figure 8:
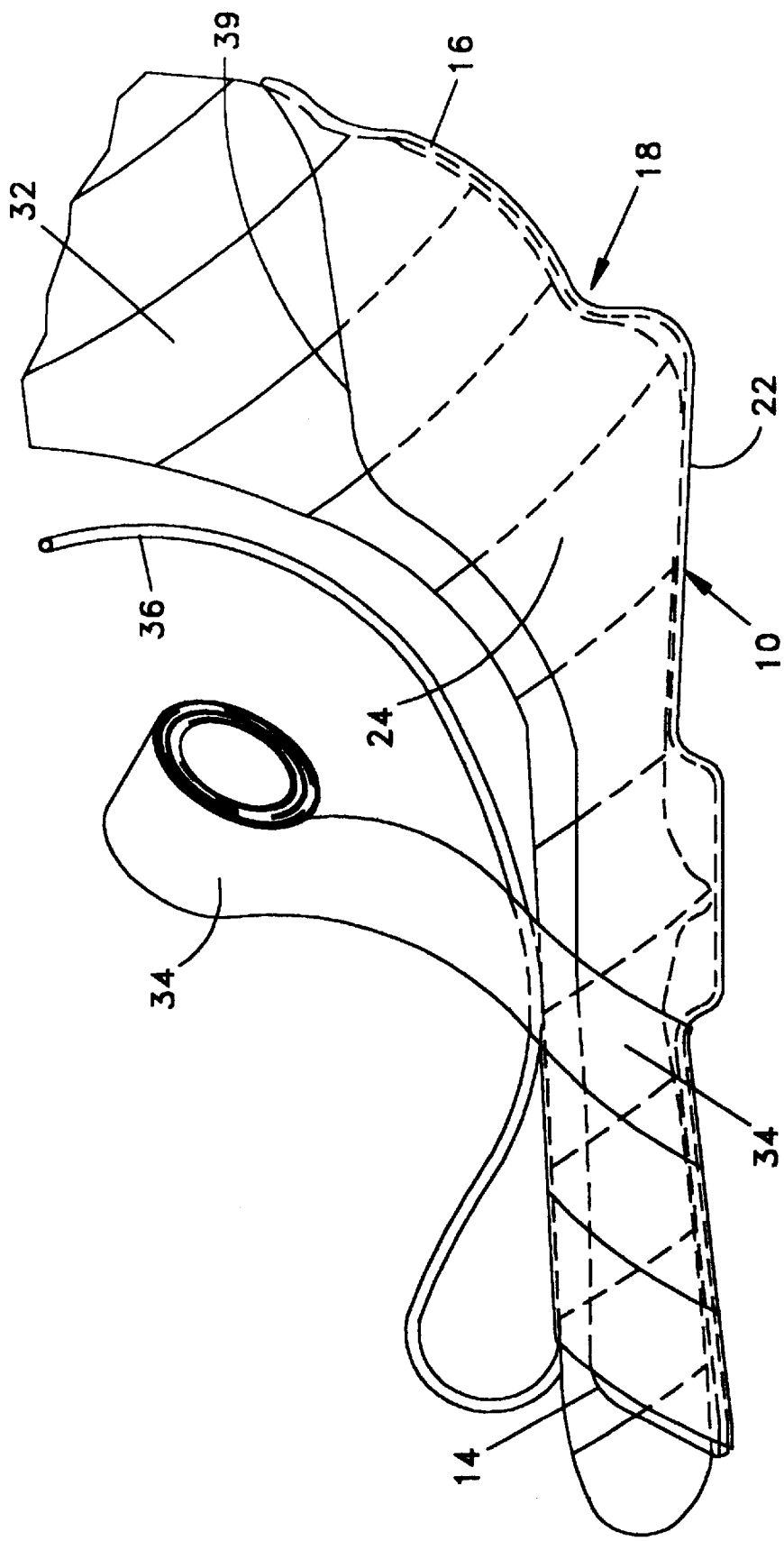
FIG. 8 is an elevational view of the splint of the present invention.

As seen in FIG. 8, the leg of a dog is shown to be positioned in the splint 10 after a wrapping of gauze bandage 32 has been placed on the leg. The wrapping of gauze bandage protects the leg and provides a snug fit between the leg and the splint. A second tape of winding 34 (such as FLEXUS tape) is then wrapped around the leg and splint together to restrain the leg from movement in the splint. It should be noted that raised portions 39 and 41 of the splint are sufficiently high enough relative to the cranial surface of the leg of the animal so that when the winding or wrapping 34 is wound around the splint and over the raised portions 39 and 41, the compressive force of the wrapping on the cephalic vein minimized at this point. An intravenous tube 36 (FIG. 8) is shown to be extending from the catheter (not shown) to the source of intravenous fluid (not shown). The IV tubing is attached to the catheter and extends distally down the leg and is then taped to the outer wrap. This allows a certain amount of "pull" on the tubing without interfering with the catheter.

The veterinarian can place the splint anytime after the catheter is in place. The device holds the elbow at around 120–140 degrees. It is difficult for the patient to pull his leg out of the splint because of the unique approach to fixing the elbow in place as discussed supra. The patient's anatomy is used to trap the elbow. If desired, a folded 4×4 inch gauze sponge may be placed over the cranial face of the elbow to additionally pad the cephalic vein. Also, as stated above to be effective the side pieces of the splint must come up high enough on the forearm to prevent restriction of the cephalic vein by the tape or the elastic bandage.

Although the splint, as disclosed herein, is described as used in conjunction with the administration of intravenous fluids to animals, this is not to be construed in a limiting sense, since other uses may be resorted to, if desired. For example, the splint may be used for fracture repair such as radial ulnar fractures. In this case, the splint prevents movement of the joint below (carpus), and joint above, the elbow. The splint "fixes" (holds still) the joint above and the joint below the fracture to gain stability for healing.

While a specific embodiment of the present invention is described hereinabove, it is to be understood that various modifications may be resorted to that is within the spirit and scope of the appended claims. For example, the tape 32 which is shown as being wrapped around the splint and leg may be replaced by straps which may or may not be integral with the splint body.

I claim:

1. A veterinary medical leg splint for an animal comprising:

a body having an elongated body portion having a first open end and a second closed end, said second closed end forming an elbow trap defined by an upstanding rear end portion having an inner curved surface which is curved to conform to the shape of the olecranon area of the animal at the elbow to snugly engage and support the olecranon area of the leg of the animal, said elbow trap including an inwardly extending shoulder on said inner surface of said upstanding rear portion and an outwardly curved depressed area disposed on said inner surface adjacent said inwardly depending shoulder, said shoulder disposed for engaging and supporting the extensor tendon of the animal's leg and, for urging the extensor tendon slightly cranial for support thereof in said outwardly curved depressed area; and restraining means for securing and restraining the leg in said splint while retaining the elbow portion of the leg in snug-fitting engagement in said support means.

2. A veterinary medical leg splint as set forth in claim 1 wherein said elongated body portion includes a downwardly depending portion having a cavity to receive the accessory carpal bone and pad of the animal therein.

3. A veterinarian medical splint as set forth in claim 1 wherein said first open end is enlarged to receive the digital and metacarpal pads of the animal's foot therein.

4. A veterinary medical splint as set forth in claim 3 wherein said first open end portion is disposed in downwardly sloped, predetermined angular relation relative to the remainder of said elongated body portion.

5. A veterinary medical splint as set forth in claim 1 wherein said first open end portion is enlarged to receive pads of the animal's foot therein.

6. A veterinary medical splint as set forth in claim 5 wherein said first open end portion is disposed in downwardly sloped, predetermined angular relation relative to the remainder of said elongated body portion.

7. A veterinary medical leg splint as in claim 1 wherein said elongated body portion includes a pair of spaced upstanding side members, each having a raised area proximal said elbow trap.

8. A veterinary leg splint as in claim 7 wherein said splint is disposed for retaining the leg therein for the administration of intravenous fluids in the cephalic vein of said leg and wherein said restraining means for securing the leg in said splint includes flexible wrapping means disposed for wrapped relation of the leg and side members of said elongated body portion including said raised areas proximal said elbow trap, whereby responsive to said flexible wrapping means being wrapped around said raised areas, pressure on the cephalic vein from the wrapping is minimized.

9. A veterinary medical leg splint as in claim 1 wherein said restraining means snugly restrains the leg in said splint to prevent relative movement between the joint above and below the elbow to provide stability to the leg for healing of radial/ulnar fractures.

10. A veterinary medical leg splint as in claim 9 wherein said restraining means includes flexible wrapping means disposed for wrapped relation of the leg and side members of said elongated body portion.

* * * * *